US012643125B2

(12) United States Patent
Fu et al.

(10) Patent No.: US 12,643,125 B2
(45) Date of Patent: Jun. 2, 2026

(54) METHOD FOR SEALING DISTAL END OF OCT CATHETER AND OCT CATHETER

(71) Applicant: SUZHOU MICROPORT ARGUS MEDICAL CORP, Jiangsu (CN)

(72) Inventors: Yuqi Fu, Jiangsu (CN); Zhenying Wu, Jiangsu (CN); Lintao Zhang, Jiangsu (CN)

(73) Assignee: SUZHOU MICROPORT ARGUS MEDICAL CORP, Jiangsu (CN)

( * ) Notice: Subject to any disclaimer, the term of this patent is extended or adjusted under 35 U.S.C. 154(b) by 276 days.

(21) Appl. No.: 18/283,957

(22) PCT Filed: Mar. 10, 2022

(86) PCT No.: PCT/CN2022/080176
§ 371 (c)(1),
(2) Date: Sep. 25, 2023

(87) PCT Pub. No.: WO2022/199396
PCT Pub. Date: Sep. 29, 2022

(65) Prior Publication Data
US 2024/0165658 A1     May 23, 2024

(30) Foreign Application Priority Data
Mar. 25, 2021     (CN) ......................... 202110321785.2

(51) Int. Cl.
*B05D 1/26*          (2006.01)
*A61M 25/00*          (2006.01)
(Continued)

(52) U.S. Cl.
CPC ........... *B05D 1/26* (2013.01); *A61M 25/0067* (2013.01); *B05D 3/067* (2013.01); *F16J 15/14* (2013.01)

(58) Field of Classification Search
CPC ......... B05D 1/26; B05D 3/067; A61M 25/001
See application file for complete search history.

(56) References Cited

U.S. PATENT DOCUMENTS

2011/0077463 A1     3/2011   Hirota
2016/0354111 A1     12/2016  Miyagawa et al.

FOREIGN PATENT DOCUMENTS

CN          103191516          7/2013
CN          104053471          9/2014
(Continued)

OTHER PUBLICATIONS

Extended European Search Report issued Aug. 19, 2024 in European Patent Application No. 22774058.6.
(Continued)

*Primary Examiner* — Rochelle D Turchen
(74) *Attorney, Agent, or Firm* — Wenderoth, Lind & Ponack, L.L.P

(57)          ABSTRACT

The present application discloses a method for sealing a distal end of an OCT catheter, comprising the following steps: dispensing an adhesive for the first time, passing an adhesive dispensing needle through the OCT catheter from a recessed hole section to dispense an adhesive in the direction of a filling section, the adhesive entering the filling section in the OCT catheter; curing for the first time, irradiating a filling portion subjected to adhesive dispensing for the first time by using an ultraviolet lamp, and curing to form a first sealant; dispensing an adhesive for the second time, enabling the adhesive dispensing needle to be close to a solidified end surface subjected to adhesive dispensing for the first time to dispense an adhesive; and curing for the second time, placing the position subjected to adhesive dispensing for the second time under the ultraviolet lamp for irradiation, curing to form a second sealant having an inclined surface, and completing sealing the distal end of the
(Continued)

OCT catheter after curing. The present application also provides an OCT catheter. The method for sealing the distal end of the OCT catheter provided by the present application is simple in operation. According to the prepared OCT catheter, during the operation, a guide wire can easily pass through a recessed hole, and is not easily blocked by the first sealant and the second sealant, such that it is convenient for the doctor to operate during the operation, and the operation time is saved.

18 Claims, 1 Drawing Sheet

(51) Int. Cl.
  *B05D 3/06*    (2006.01)
  *F16J 15/14*    (2006.01)

(56) References Cited

FOREIGN PATENT DOCUMENTS

| CN | 105188833 | 12/2015 |
| CN | 106413592 | 2/2017 |
| CN | 108289690 | 7/2018 |
| CN | 208524844 | 2/2019 |
| CN | 112495704 | 3/2021 |
| CN | 113083633 | 7/2021 |
| EP | 2 808 051 | 12/2014 |
| EP | 3 103 403 | 12/2016 |
| EP | 3 395 270 | 10/2018 |

OTHER PUBLICATIONS

International Search Report issued Jun. 8, 2022, by the China National Property Administration as the ISA, in International (PCT) Application No. PCT/CN2022/080176.

METHOD FOR SEALING DISTAL END OF OCT CATHETER AND OCT CATHETER

FIELD OF THE INVENTION

The present application relates to the technical field of optical interference tomography, and specifically relates to a method for sealing the distal end of an OCT catheter and an OCT catheter.

BACKGROUND OF THE INVENTION

Optical coherence tomography (OCT) is a new type of tomographic imaging technology that has developed rapidly in recent years and has the most promising prospects, especially biopsy and imaging of biological tissues. It has been tried to be applied in clinical diagnosis of cardiology, ophthalmology, dentistry and dermatology. It is another major technological breakthrough after X-CT and MRI technology. In recent years, it has been developed rapidly. The optical interference tomography system based on this technology can enable people to obtain ultra-high-definition images with spatial resolution on the order of microns. When the imaging catheter used for optical interference tomography imaging system scanning is used to seal the distal end of the catheter, in order to seal the catheter, a section of ultraviolet adhesive needs to be injected into the guide wire hole and cured. The existing operation generally adopts the following method: the operator uses a dispensing machine, and after dispensing and molding at one time, uses an ultraviolet lamp to irradiate and cure.

The existing adhesive dispensing method has the following disadvantages: after one dispensing, due to the surface tension of the liquid, after the ultraviolet adhesive is cured and molded, the end faces at both ends are almost at right angles. When the OCT catheter is actually used, the distal end needs to pass through a 0.014" guide wire, the right-angled end face of the ultraviolet adhesive can easily obstruct the guide wire, making it difficult for the guide wire to pass through, affecting the doctor's feel and delaying the operation time.

SUMMARY OF THE INVENTION

In view of the above problems, the present application provides a method for sealing the distal end of an OCT catheter and an OCT catheter. During surgery, the guide wire can easily pass through the catheter and is not easily obstructed, which makes it easy for doctors to operate during surgery and saves operation time.

The application provides the following technical solutions.

1. A method for sealing the distal end of an OCT catheter, comprising the following steps:

dispensing an adhesive for the first time, passing an adhesive dispensing needle through the OCT catheter from a recessed hole section to dispense an adhesive in the direction of a filling section, the adhesive entering the filling section inside the OCT catheter, curing for the first time, irradiating the filling section after the first dispensing by using an ultraviolet lamp, and curing to form a first sealant;

dispensing an adhesive for the second time, enabling the adhesive dispensing needle to be close to a solidified end surface after the first dispensing time to dispense an adhesive;

curing for the second time, placing the position after the second dispensing under the ultraviolet lamp for irradiation, curing to form the second sealant having an inclined surface, and completing sealing the distal end of the OCT catheter after curing.

2. The method for sealing the distal end of an OCT catheter according to claim 1, wherein the adhesive used in the adhesive dispensing for the first time and the adhesive dispensing for the second time is ultraviolet adhesive.

3. The method for sealing the distal end of an OCT catheter according to claim 1, wherein the dispensing pressure of the adhesive dispensing for the first time is 6-8 kg/cm$^2$, preferably 7 kg/cm$^2$, and the time of adhesive dispensing is 0.15-0.25 s, preferably 0.2 s;

the dispensing pressure of the adhesive dispensing for the second time is 1-3 kg/cm$^2$, preferably 2 kg/cm$^2$, and the time of adhesive dispensing is 0.15-0.25 s, preferably 0.2 s.

4. The method for sealing the distal end of an OCT catheter according to claim 1, wherein the time of curing for the first time is 5-15 s, preferably 8 s; the time of curing for the second time is 5-15 s, preferably 8 s.

5. The method for sealing the distal end of an OCT catheter according to claim 1, wherein the end of the first sealant connected to the recessed hole section is the first end, and the end far from the recessed hole section is the second end, the second sealant is connected to the first end of the first sealant, and the second sealant has an inclined surface, and the inclined surface is at least partially located within the recessed hole section.

6. The method for sealing the distal end of an OCT catheter according to claim 11, wherein the recessed hole section comprises a recessed hole and a first space located below the recessed hole, and the recessed hole has a bottom end and a top end, the bottom end of the recessed hole is connected to the first end of the first sealant, and the top end of the recessed hole is away from the first sealant.

7. The method for sealing the distal end of an OCT catheter according to claim 6, wherein the radial size of the first space gradually increases in the axial direction from the bottom end to the top end.

8. The method for sealing the distal end of an OCT catheter according to claim 6, wherein the second sealant is at least partially located within the first space.

9. The method for sealing the distal end of an OCT catheter according to claim 5, wherein the first end surface and the second end surface of the first sealant are both perpendicular to the tube wall.

10. The method for sealing the distal end of an OCT catheter according to claim 6, wherein the included angle between the inclined surface and the tube wall below the recessed hole does not exceed 60°, preferably 45°.

11. An OCT catheter, wherein the OCT catheter has a recessed portion, the recessed portion includes a filling section and a recessed hole section, and the radial size of the filling section gradually decreases in the direction close to the recessed hole section in the axial direction until it connects with the recessed hole section, the filling section is filled with a first sealant, and the end of the first sealant connected to the recessed hole section is the first end, the end away from the recessed hole section is the second end, a second sealant is connected to the first end of the first sealant, and the second sealant has an inclined surface, and the inclined surface is at least partially located within the recessed hole section.

12. The OCT catheter according to claim 11, wherein the recessed hole section comprises a recessed hole and a first space located below the recessed hole, the recessed hole has a bottom end and a top end, and the bottom end of the recessed hole is connected with the first end of the first sealant, and the top end of the recessed hole is away from the first sealant.

13. The OCT catheter according to claim 12, wherein a radial size of the first space gradually increases in an axial direction from the bottom end to the top end.

14. The OCT catheter according to claim 12, wherein the second sealant is at least partially located within the first space.

15. The OCT catheter according to claim 11, wherein the first end surface and the second end surface of the first sealant are both perpendicular to the tube wall.

16. The OCT catheter according to claim 12, wherein the included angle between the inclined surface and the tube wall below the recessed hole does not exceed 60°.

17. The OCT catheter according to claim 12, wherein the included angle between the inclined surface and the tube wall below the recessed hole is 45°.

18. The OCT catheter according to claim 11, wherein the OCT catheter is prepared by the method described in any one of claims 1-10.

The method for sealing the distal end of an OCT catheter provided by this application is simple to operate. The guide wire of the prepared OCT catheter can easily pass through the recessed hole during the operation and is not easily obstructed by the first sealant and the second sealant, which makes it easy for doctors to operate during surgery and saves operation time.

BRIEF DESCRIPTION OF THE DRAWINGS

The accompanying drawings are used for better understanding of the present application, and do not constitute an improper limitation of the present application.
wherein.

DESCRIPTION OF REFERENCE NUMERALS

Figure 1:
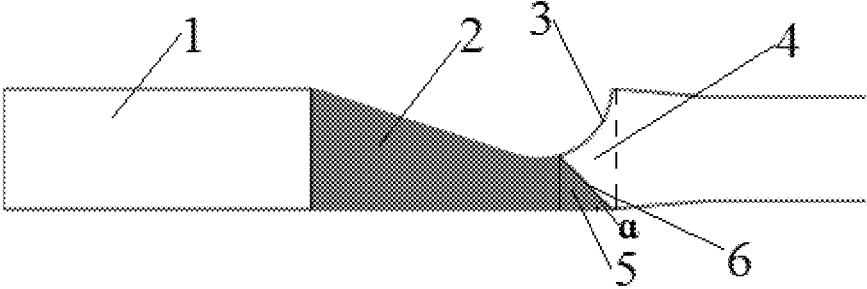
FIG. 1 is a schematic structural diagram of the OCT catheter provided by this application.

1—OCT catheter, 2—first sealant, 3—recessed hole, 4—first space, 5—second sealant, 6—inclined surface, 7—guide wire.

DETAIL DESCRIPTION OF THE INVENTION

The following describes the exemplary embodiments of the present application, including various details of the embodiments of the present application to facilitate understanding, and they should be considered as exemplary only. Accordingly, those of ordinary skilled in the art will recognize that various changes and modifications of the embodiments described herein can be made without departing from the scope and spirit of the present application. Also, descriptions of well-known functions and constructions are omitted from the following description for clarity and conciseness.

The present application provides a method for sealing the distal end of an OCT catheter, comprising the following steps:

Step 1: dispensing an adhesive for the first time, passing an adhesive dispensing needle through the OCT catheter from a recessed hole section to dispense an adhesive in the direction of a filling section, the adhesive entering the filling section inside the OCT catheter, Step 2: curing for the first time, irradiating the filling section after the first dispensing by using an ultraviolet lamp, and curing to form the first sealant;

Step 3: dispensing an adhesive for the second time, enabling the adhesive dispensing needle to be close to a solidified end surface after the first dispensing to dispense an adhesive;

Step 4: curing for the second time, placing the position after the second dispensing under the ultraviolet lamp for irradiation, curing to form the second sealant having an inclined surface, and completing sealing the distal end of the OCT catheter after curing.

The adhesive used in adhesive dispensing for the first time and adhesive dispensing for the second time is ultraviolet adhesive; for example, Dymax 1201-M-SC, Dymax 1202-M-SC, and Dymax 1204-M-SC.

The ultraviolet adhesive used for adhesive dispensing for the first time is in the filling section. Due to the gravitational force of the upper and lower tube walls in the filling section on the ultraviolet adhesive, the ultraviolet adhesive will not flow freely in the filling section, so that after curing, both ends of the first sealant are perpendicular to the upper and lower pipe walls or tangents of the upper and lower pipe walls in the filling section that are connected to the first sealant.

In this application, the dispensing pressure of adhesive dispensing for the first time is 6-8 kg/cm², preferably 7 kg/cm², and the time of adhesive dispensing is 0.15-0.25 s, preferably 0.2 s;

The dispensing pressure of adhesive dispensing for the first time can be 6 kg/cm², 6.1 kg/cm², 6.2 kg/cm², 6.3 kg/cm², 6.4 kg/cm², 6.5 kg/cm², 6.6 kg/cm², 6.7 kg/cm², 6.8 kg/cm², 6.9 kg/cm², 7 kg/cm², 7.1 kg/cm², 7.2 kg/cm², 7.3 kg/cm², 7.4 kg/cm², 7.5 kg/cm², 7.6 kg/cm², 7.7 kg/cm², 7.8 kg/cm², 7.9 kg/cm², 8 kg/cm².

The time of adhesive dispensing for the first time can be 0.15 s, 0.16 s, 0.17 s, 0.18 s, 0.19 s, 0.2 s, 0.21 s, 0.22 s, 0.23 s, 0.24 s, 0.25 s.

The dispensing pressure of adhesive dispensing for the second time is 1-3 kg/cm², preferably 2 kg/cm², and the time of adhesive dispensing is 0.15-0.25 s, preferably 0.2 s.

The dispensing pressure of adhesive dispensing for the second time can be 1 kg/cm², 1.1 kg/cm², 1.2 kg/cm², 1.3 kg/cm², 1.4 kg/cm², 1.5 kg/cm², 1.6 kg/cm², 1.7 kg/cm², 1.8 kg/cm², 1.9 kg/cm², 2 kg/cm², 2.1 kg/cm², 2.2 kg/cm², 2.3 kg/cm², 2.4 kg/cm², 2.5 kg/cm², 2.6 kg/cm², 2.7 kg/cm², 2.8 kg/cm², 2.9 kg/cm², 3 kg/cm².

The time of adhesive dispensing for the second time can be 0.15 s, 0.16 s, 0.17 s, 0.18 s, 0.19 s, 0.2 s, 0.21 s, 0.22 s, 0.23 s, 0.24 s, 0.25 s.

The first curing time is 5-15 s, preferably 8 s; the second curing time is 5-15 s, preferably 8 s.

The ratio of the first dispensing amount to the second dispensing amount is (2-8):1.

As shown in FIG. 1, the OCT catheter 1 of the present application has a recessed portion, which comprises a filling section and a recessed hole section. The radial size of the filling section gradually decreases in the direction axially close to the recessed hole section, until it connects with the recessed hole section, the filling section is filled with a first sealant 2, and the end of the first sealant 2 connected to the recessed hole section is the first end, the end far from the recessed hole section is the second end, the first end of the first sealant 2 is connected with a second sealant 5, and the second sealant 5 has an inclined surface 6, and the inclined surface 6 is at least partially located within the recessed hole section.

The first sealant 2 fills the filling section, and the first sealant 2 and the second sealant 5 form a sealing layer to seal the distal end of the OCT catheter 1. Moreover, due to the inclined surface 6 of the second sealant 5, during the operation, the guide wire 7 can easily pass through the recessed hole section along the inclined surface 6, and the guide wire 7 will not be easily obstructed by the second sealant 5, thereby improving the efficiency of doctors' surgeries.

The recessed hole section comprises a recessed hole 3 and a first space 4 located below the recessed hole 3, the recessed hole 3 has a bottom end and a top end, and the bottom end of the recessed hole 3 is connected to the first end of the first sealant 2, and the top end of the recessed hole 3 is away from the first sealant 2. The radial size of the first space 4 gradually increases in the axial direction from the bottom end to the top end. The radial size of the first space 4 at the bottom end of the recessed hole 3 is consistent with the radial size of the first end of the first sealant 2, and the radial size of the first space 4 at the top end of the recessed hole 3 is consistent with the inner diameter of the OCT catheter 1.

The second sealant 5 is at least partially located within the first space 4.

In a specific embodiment, the inclined surface 6 of the second sealant 5 can extend through the first space 4 to the distal end of the OCT catheter 1.

In another specific embodiment, the inclined surface 6 of the second sealant 5 is located within the first space 4.

The included angle α between the inclined surface 6 and the tube wall below the recessed hole 3 does not exceed 60°, that is, the included angle α between the inclined surface 6 and the tube wall below the first space 4 does not exceed 60°, preferably 45°. In actual situations, the included angle α can be 60°, 59°, 58°, 57°, 56°, 55°, 54°, 53°, 52°, 51°, 50°, 49°, 48°, 47°, 46°, 45°, 44°, 43°, 42°, 41°, 40°, 39°, 38°, 37°, 36°, 35°, 34°, 33°, 32°, 31°, 30°, etc.

Figure 2:
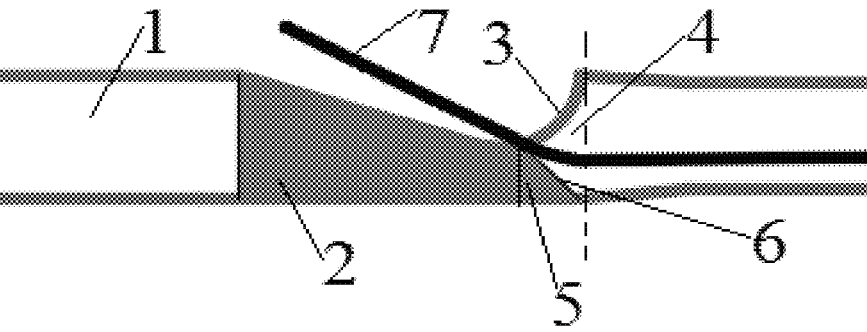
FIG. 2 is a schematic structural diagram of the OCT catheter provided by this application when used.

As shown in FIG. 2, when the OCT catheter described in the present application is used, the guide wire 7 passes through the distal end of the OCT catheter 1. When the guide wire 7 reaches the first space 4, the guide wire 7 reaches the recessed hole 3 along the inclined surface 6 of the second sealant 5 and passes through the recessed hole 3. The first sealant 2 and the second sealant 5 not only separate the distal and proximal ends of the catheter, and the inclined surface 6 of the second sealant is conducive to the penetration of the guide wire 7, so that the doctor can improve the operating efficiency during surgery.

Although the embodiments of the present application have been described above, the present application is not limited to the above-mentioned specific embodiments and application fields, and the above-mentioned specific embodiments are only illustrative, instructive, rather than restrictive. Those ordinary skilled in the art can also make many forms under the enlightenment of this description and without departing from the protection scope of the claims of the present application, and these all belong to the protection scope of the application.

The invention claimed is:

1. A method for sealing a distal end of an Optical Coherence Catheter (OCT catheter), comprising the following steps:
dispensing an adhesive for a first time, comprising passing an adhesive dispensing needle through the OCT catheter from a recessed hole section to dispense the adhesive in the direction of a filling section, the adhesive entering the filling section inside the OCT catheter, curing for a first time, comprising irradiating the filling section after the first dispensing by using an ultraviolet lamp, and curing to form a first sealant;
dispensing an additional adhesive for a second time, comprising enabling the adhesive dispensing needle to be close to a solidified end surface after the first dispensing time to dispense the additional adhesive;
curing for a second time, comprising placing the position of the OCT catheter which is dispensed with the additional adhesive under the ultraviolet lamp for irradiation, curing to form a second sealant having an inclined surface, and completing sealing the distal end of the OCT catheter after curing.

2. The method for sealing the distal end of the OCT catheter according to claim 1, wherein the adhesive used in the adhesive dispensing for the first time and the additional adhesive used in the additional adhesive dispensing for the second time is each an ultraviolet adhesive.

3. The method for sealing the distal end of the OCT catheter according to claim 1, wherein in the adhesive dispensing for the first time, a dispensing pressure is 6-8 $kg/cm^2$, and a time of adhesive dispensing is 0.15-0.25 s; and
in the additional adhesive dispensing for the second time, a dispensing pressure is 1-3 $kg/cm^2$, and a time of adhesive dispensing is 0.15-0.25 s.

4. The method for sealing the distal end of the OCT catheter according to claim 1, wherein a time of curing for the first time is 5-15 s; and a time of curing for the second time is 5-15 s.

5. The method for sealing the distal end of the OCT catheter according to claim 1, wherein the first sealant is connected to the recessed hole section, an end of the first sealant connected to the recessed hole section is the first end, and an end opposite from the recessed hole section is the second end, and
the second sealant is connected to the first end of the first sealant, and the second sealant has an inclined surface, and the inclined surface is at least partially located within the recessed hole section.

6. The method for sealing the distal end of the OCT catheter according to claim 1, wherein the recessed hole section comprises a recessed hole and a first space located below the recessed hole, and the recessed hole has a bottom end and a top end, the bottom end of the recessed hole is connected to a first end of the first sealant, and the top end of the recessed hole is away from the first sealant.

7. The method for sealing the distal end of the OCT catheter according to claim 6, wherein a radial size of the first space gradually increases in an axial direction from the bottom end to the top end.

8. The method for sealing the distal end of the OCT catheter according to claim 6, wherein the second sealant is at least partially located within the first space.

9. The method for sealing the distal end of the OCT catheter according to claim 5, wherein the first end surface and the second end surface of the first sealant are both perpendicular to a tube wall of the OCT catheter.

10. The method for end of the OCT catheter according to claim 6, wherein an included angle between the inclined surface and a wall of the OCT catheter below the recessed hole does not exceed 60°.

11. An Optical Coherence Catheter (OCT catheter), comprising a recessed portion, the recessed portion includes a filling section and a recessed hole section, and a radial size of the filling section gradually decreases in a direction close to the recessed hole section in an axial direction until it connects with the recessed hole section, the filling section is filled with a first sealant, and the first sealant is connected the recessed hole section, an end of the first sealant connected to the recessed hole section is a first end, an end opposite from the recessed hole section is a second end, a second sealant is connected to the first end of the first sealant, and the second sealant has an inclined surface, and the inclined surface is at least partially located within the recessed hole section.

12. The OCT catheter according to claim 11, wherein the recessed hole section comprises a recessed hole and a first space located below the recessed hole, the recessed hole has a bottom end and a top end, and the bottom end of the recessed hole is connected with the first end of the first sealant, and the top end of the recessed hole is away from the first sealant.

13. The OCT catheter according to claim 12, wherein a radial size of the first space gradually increases in an axial direction from the bottom end to the top end.

14. The OCT catheter according to claim 12, wherein the second sealant is at least partially located within the first space.

15. The OCT catheter according to claim 11, wherein the first end surface and the second end surface of the first sealant are both perpendicular to a tube wall of the OCT catheter.

16. The OCT catheter according to claim 12, wherein an included angle between the inclined surface and a tube wall of the OCT catheter below the recessed hole does not exceed 60°.

17. The OCT catheter according to claim 12, wherein an included angle between the inclined surface and a tube wall of the OCT catheter below the recessed hole is 45°.

18. The OCT catheter according to claim 11, wherein the OCT catheter is prepared by a method comprising:

dispensing an adhesive for a first time, comprising passing an adhesive dispensing needle through the OCT catheter from the recessed hole section to dispense the adhesive in the direction of the filling section, the adhesive entering the filling section inside the OCT catheter, curing for a first time, comprising irradiating the filling section after the first dispensing by using an ultraviolet lamp, and curing to form a first sealant;

dispensing an additional adhesive for a second time, comprising enabling the adhesive dispensing needle to be close to a solidified end surface after the first dispensing time to dispense the additional adhesive;

curing for a second time, comprising placing the position of the OCT catheter which is dispensed with the additional adhesive under the ultraviolet lamp for irradiation, curing to form a second sealant having an inclined surface, and completing sealing a distal end of the OCT catheter after curing.

* * * * *